(12) United States Patent
Eketorp et al.

(10) Patent No.: US 6,767,405 B2
(45) Date of Patent: Jul. 27, 2004

(54) APPARATUS AND PROCESS FOR COATING ARTICLES

(75) Inventors: Rainer Eketorp, Danderyd (SE); Per Tornblad, Bromma (SE)

(73) Assignee: Carmeda AB, Upplands-Vasby (SE)

( * ) Notice: Subject to any disclaimer, the term of this patent is extended or adjusted under 35 U.S.C. 154(b) by 183 days.

(21) Appl. No.: 10/191,450

(22) Filed: Jul. 10, 2002

(65) Prior Publication Data

US 2004/0009288 A1 Jan. 15, 2004

(51) Int. Cl.[7] ............................................. B05C 3/109
(52) U.S. Cl. ..................... 118/411; 118/412; 118/429; 118/500; 422/99; 422/102; 422/104
(58) Field of Search ................. 118/411, 412, 118/429, 500; 422/99, 100, 101, 102, 103, 104; 206/49.1; 211/49.1, 59.4, 126.2, 126.3; 134/137, 142, 168 C, 167 C, 169 C; 137/575, 576

(56) References Cited

U.S. PATENT DOCUMENTS

| 3,576,176 A | * | 4/1971 | Pickett ........................ 118/500 |
| 4,427,027 A | * | 1/1984 | Miyahara et al. ........... 137/576 |
| 4,427,415 A | * | 1/1984 | Cleveland .................... 436/57 |
| 4,569,647 A | * | 2/1986 | McCormick ................. 425/117 |
| 4,777,021 A | * | 10/1988 | Wertz et al. ................. 422/101 |
| 5,080,869 A | * | 1/1992 | McCormick ................. 422/102 |

FOREIGN PATENT DOCUMENTS

| EP | 0 086 186 A1 | 8/1983 |
| EP | 0 495 820 B1 | 7/1992 |
| EP | 1 029 654 A2 | 8/2000 |
| EP | 1 300 197 A2 | 4/2003 |
| WO | 91/05817 A1 | 5/1991 |
| WO | 97/13635 A1 | 4/1997 |

* cited by examiner

*Primary Examiner*—Laura Edwards
(74) *Attorney, Agent, or Firm*—Burns, Doane, Swecker & Mathis, L.L.P.

(57) ABSTRACT

An apparatus and process for coating a plurality of articles in batches, in particular for applying a biocompatible layer on articles adapted to come into contact with blood or body tissue, e.g. a coagulation-preventing substance so as to render the articles non-thrombogenic. A plurality of article-carrying plates (14) are stacked upon one another and have a plurality of communicating wells (18) for receiving therein a respective article to be coated. A base plate (12) defines with a bottom side of a lowermost of said article-carrying plates a distribution chamber (34) for receiving and evenly distributing a solution containing a substance to be applied to said articles. The solution is fed through the wells of the stacked plates (14) in parallel vertical flows.

17 Claims, 3 Drawing Sheets

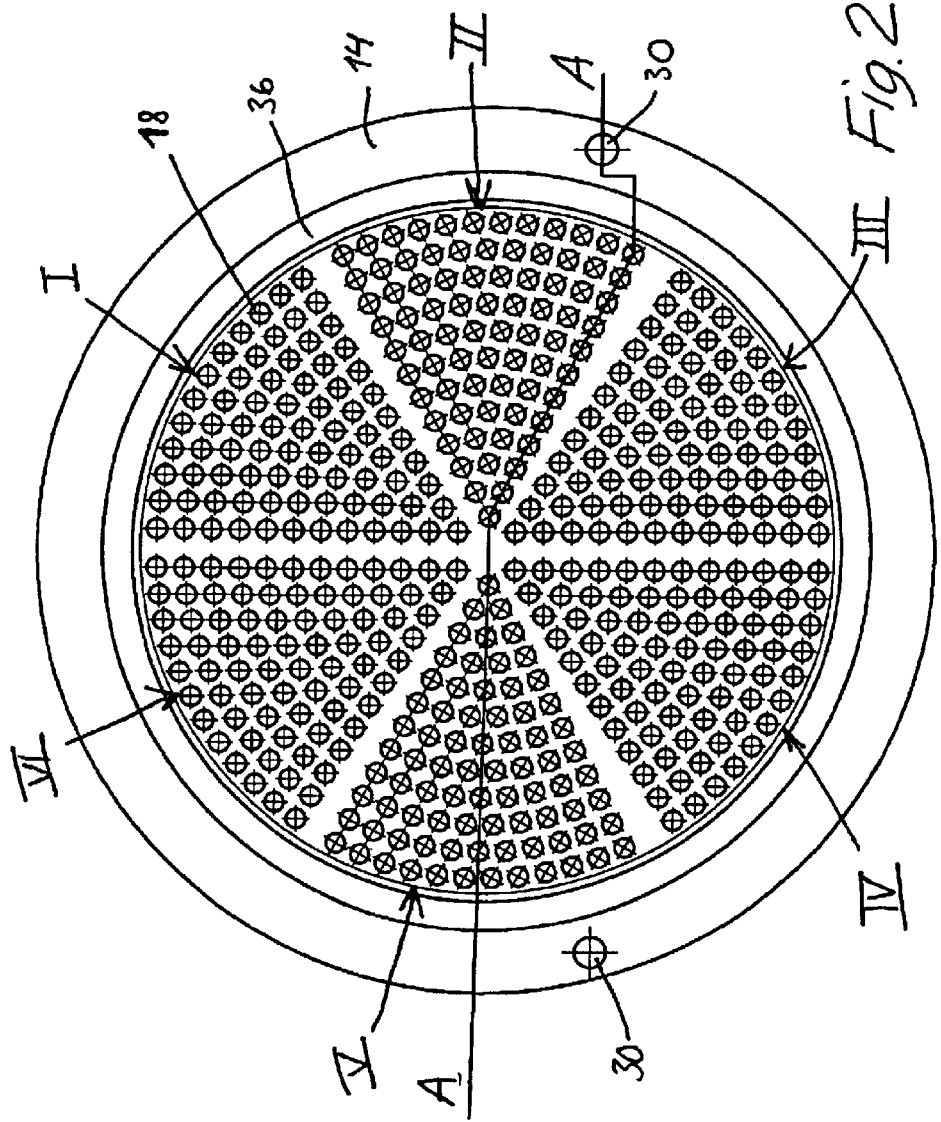

_US 6,767,405 B2_

APPARATUS AND PROCESS FOR COATING ARTICLES

BACKGROUND OF THE INVENTION

1. Field of the Invention

The present invention relates generally to an apparatus for coating a plurality of articles in batches. In particular, the invention relates to an apparatus for applying a biocompatible layer on articles adapted to come into contact with blood or body tissue, e.g. a coagulation-preventing substance so as to render the articles non-thrombogenic.

The invention also relates to a process for coating a plurality of articles in batches, in particular for applying a biocompatible layer on articles adapted to come into contact with blood or body tissue, e.g. a coagulation-preventing substance so as to render the articles non-thrombogenic.

2. Description of Related Art

It is well known that when blood comes into contact with other materials than the fresh natural wall of the blood vessel, for example in surgery with medical instruments such as scalpels, activation of certain circulating cells and enzyme systems takes place resulting in blood coagulation. Release of blood coagels or thrombi in the blood flow could lead to thrombosis, a major cause of death in the industrialised world. Coating the surfaces of solid substrates such as medical instruments with certain polysaccharides such as heparin makes these surfaces non-thrombogenic. EP 0 086 186 B1 and EP 0 495 820 B1 describe generally methods of how to bind polysaccharides to articles in order to make the surfaces of the substrates non-thrombogenic.

Furthermore, it is known to batchwise apply a coagulation-preventing coating on endovascular stents, adapted to be implanted e.g. in coronary artery, by placing the stents in a plurality of cavities interconnected serially by a passageway through which a solution containing the substance to be applied onto the stents is supplied sequentially to the cavities and to the stents placed therein. However, such an arrangement of the cavities and the serial flow passage of the solution therethrough may give rise to cavitation problem which may affect the quality and the uniformity of the coating applied to the articles. Also, the coating capacity of such a setup is limited.

SUMMARY OF THE INVENTION

It is an object of the invention to provide an apparatus, which eliminates said drawbacks of the prior art. To this end the apparatus of the present invention comprises an article-carrying plate, said article-carrying plate having a top side and a bottom side, a plurality of wells being formed in said top side for receiving therein a respective article to be coated, each of said wells communicating, via a respective orifice, with a space below said bottom side, said orifices having each a cross-sectional flow area that is smaller than the cross-sectional area of each well; a base plate having an upper surface defining with said bottom side of said article-carrying plate a distribution chamber for receiving and evenly distributing to said orifices a solution containing the coating substance to be applied to said articles, said base plate having an inlet for supplying said solution to said chamber; and a top plate covering said top side of the article-carrying plate and defining therewith a collection chamber for receiving used solution having been flown through said orifices and wells, said top plate having an outlet for discharging said used solution.

In order to multiply the coating capacity of the apparatus a plurality of said article-carrying plates are stacked upon one another.

A further object of the invention is to provide a process for coating a plurality of articles in batches, in particular for applying a biocompatible layer on articles adapted to come into contact with blood or body tissue, said process comprising the steps of: loading at least one article-carrying plate, having a plurality of article-receiving wells, with articles to be coated; supplying a solution containing the substance to be applied to the articles to a distribution chamber upstream of and communicating with said wells of the article-carrying plate; feeding said solution in parallel vertical flows through said wells to apply a coating of said substance on the articles; and removing the articles from the wells of said article-carrying plate after completion of the coating of said articles. Preferably, to increase the coating capacity the process comprises the step of feeding said solution in parallel vertical flows through the wells of a plurality of said article-carrying plates stacked one upon the other.

Other features and particulars of the apparatus and process of the present invention will be clear from the following description and claims together with the accompanying drawings.

BRIEF DESCRIPTION OF THE DRAWINGS

FIG. 2 is a plan view of one of the article-carrying plates in FIG. 1;

DETAILED DESCRIPTION OF AN EMBODIMENT OF THE INVENTION

Figure 1:
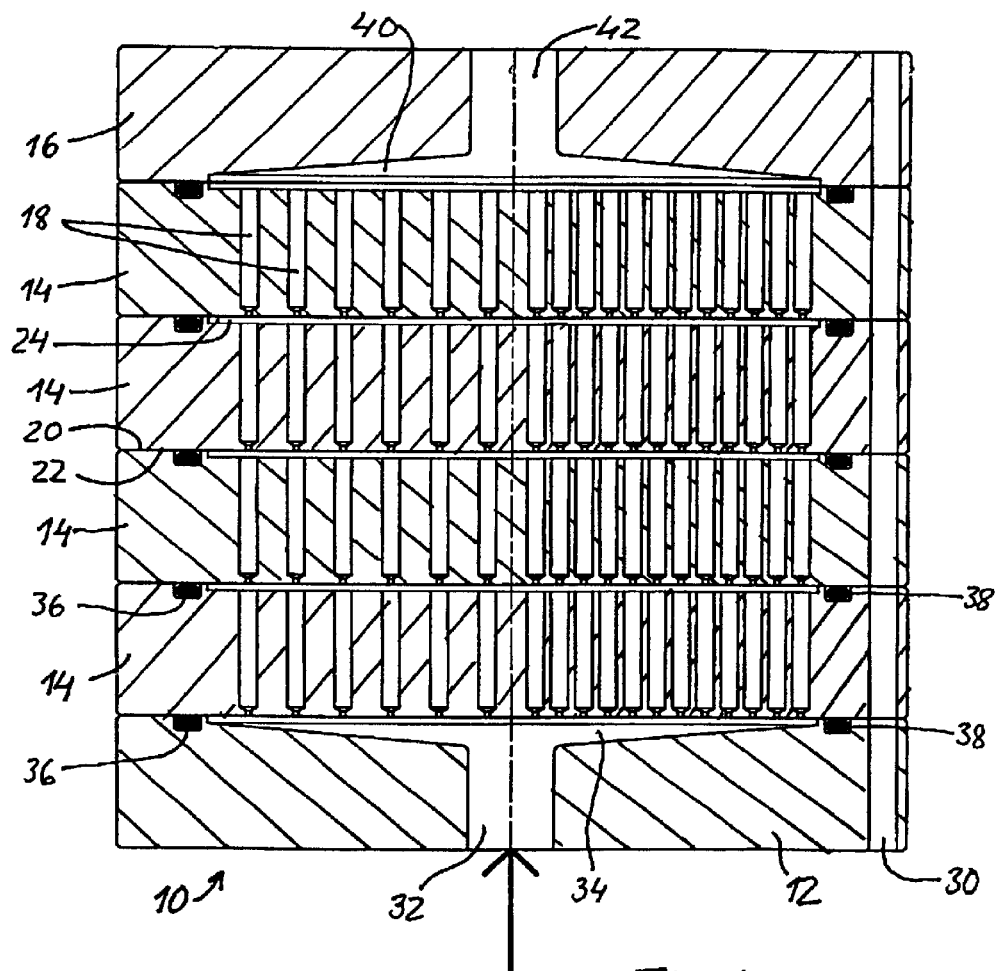
FIG. 1 is a vertical cross-sectional view of an apparatus comprising four article-carrying plates for receiving a plurality of articles to be coated with an anticoagulation substance, wherein the article-carrying plates are shown in a section according to line A—A in FIG. 2.

FIG. 1 illustrates in a cross-sectional side view an apparatus 10 of the present invention for applying, in a batchwise manner, a biocompatible coating onto a plurality of articles to be implanted into human blood vessels. Typical examples of such articles are grafts and endovascular stents, which are to be coated with a layer of a coagulation-preventing substance so as to make them non-thrombogenic. Other such articles may be various matrices for slow-release compositions.

In the embodiment shown, the apparatus 10 comprises a stack of circular disc-shaped plates, i.e. a base plate 12, four article-carrying plates 14 and a top plate 16 placed coaxially upon one another. All article-carrying plates 14 are provided with a large number of article-receiving, cylindrical wells 18, which are preferably arranged in a plurality of circular arrays and grouped in circle sectors, such as six circle sectors I, II, III, IV, V and VI, each with 78 wells, thereby to provide a polar co-ordinate system for easy identification of each well 18. The circular arrays may be designated A–L from the center and out, and the wells of the arrays may be numbered clockwise from 1 up to 12 in each sector. Thus, the well identified with 18 in FIG. 1 corresponds to a position "IL10".

The plates 12, 14 and 16 are preferably made of a plastic material, such as one selected from the group consisting of the polyamide plastic PA 12 and the acetal plastic POM (polyoxymethylene), and are chemically inert to solutions adapted to flow through the wells 18 for applying relevant coatings onto the articles placed therein. Such solutions may include a heparin solution and correspond to the ones used in Example 1 in EP 0 495 820 B1. In case a low weight of the apparatus is of less importance the plates 12, 14 and 16 may be made of any suitable metal, such as stain-less steel or titanium.

Figure 4:
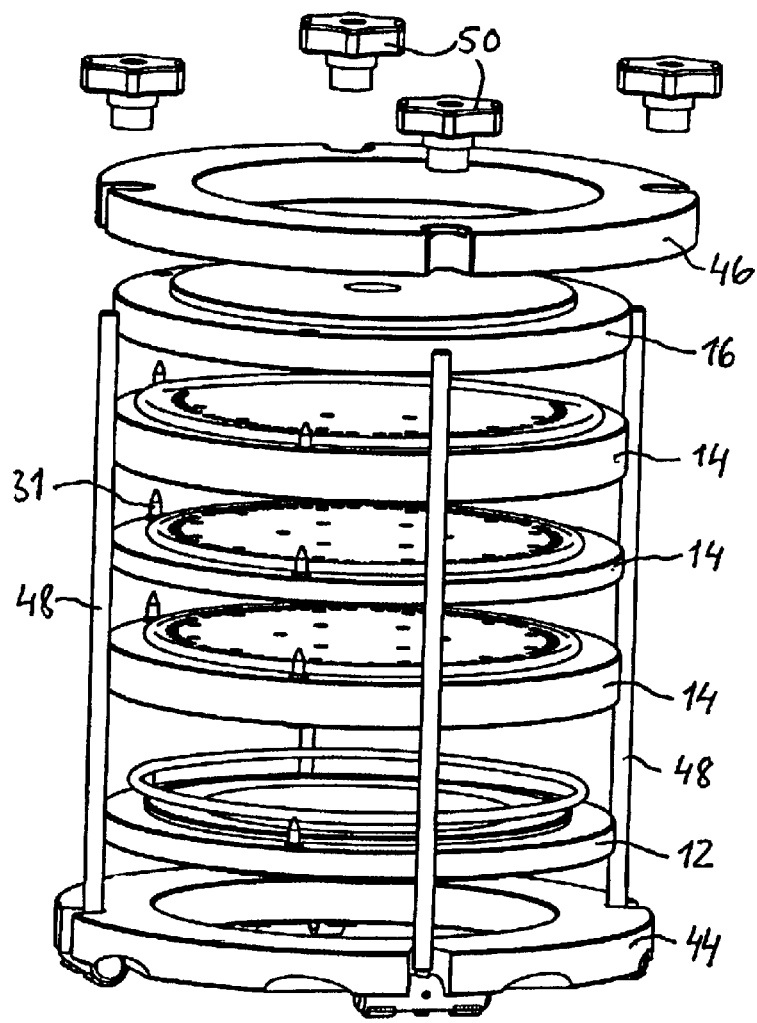
FIG. 4 is an exploded perspective view of an apparatus of the present invention having three article-carrying plates and discloses an arrangement for holding the assembly of plates together by means of a clamping device.
Figure 3:
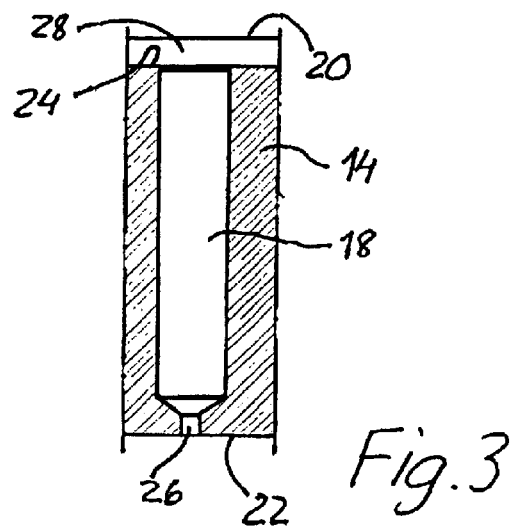
FIG. 3 illustrates an article-receiving well in an enlarged sectional view.

As best shown in FIGS. 1 and 3, each article-carrying plate 14 has a top side 20 and a bottom side 22. Each well 18 opens into a common, shallow recess 24 in the top side 20 of the plate 14 and communicates via a narrow orifice 26 with a space 28 defined by the bottom side 22 of the plate 14 and the top side 20 of an adjacent plate 14 placed underneath it. Each plate 12, 14 16 has at least two holes 30 matching with corresponding holes in the adjacent plates. These holes 30 serve for a desired mutual position of the plates when stacking the latter and may receive a respective shaft (not shown) extending through all plates 12, 14, 16. Alternatively, the holes 30 may be guide holes opening into the bottom side of the plates 14 and 16 for receiving a respective guide pin 31 (see FIG. 4) fixated in and projecting upwardly from the plates 12 and 14. The mutual position of the article-carrying plates 14 in a circumferential direction is preferably such that the wells 18 of the adjacent plates 14 are aligned in a coaxial relationship, although this is not a requisite for obtaining good flow characteristics through the wells and the spaces 28 between the article-carrying plates 14. The number of article-carrying plates 14 in the stack is optional. However, it is preferred that the stack comprises up to 25 such plates. As shown in FIG. 4, the stack may include article-carrying plates 14 of different thickness so that articles of various length may be coated in one and the same process.

The base plate 12 has a central inlet opening 32 for a solution to be supplied to the wells 18 in the plates 14. The inlet opening 32 widens into a shallow distribution chamber 34, which communicates with all wells 18 of the lowermost plate 14 via the orifices 26 so as to provide for a uniform supply of said solution to the wells 18. The top side of the plates 12 and 14 has a respective annular groove 36, which circumscribes the radially outer array of wells 18 and houses a respective O-ring 38 to provide a sealing between each pair of adjacent plates 12, 14, 16. The top plate 16 has a shallow collection chamber 40 for receiving the solution that has passed through all wells 18 of the article-carrying plates 14. The solution in the collection chamber 40 is discharged through a central outlet opening 42 of the top plate 16.

FIG. 4 illustrates a clamping arrangement for holding the assembly of plates 12, 14 and 16 together during a coating process. The arrangement comprises a lower ring-shaped plate 44 and an upper ring-shaped plate 46, between which the plates 12, 14 and 16 are hold stacked upon one another and clamped together by means of four circumferentially spaced tie rods 48. The assembly is tightened by turning knobs 50 engaging threaded upper ends of the tie rods 48. There should be at least three such tie rods 48 equally spaced circumferentially.

A process of the present invention for coating a plurality of articles, such as endovascular stents, with a layer of a biocompatible substance, e.g. a coagulation-preventing substance, such as heparin, will now be described with reference to the drawings.

Initially, the wells 18 of each plate 14 are loaded with the articles to be coated. This could be accomplished by turning the plate 14 upside down and docking the same with a complementary loading plate (not shown) filled with the articles to be coated. Then, the plate 14 and the loading plate are together turned 180° so that the articles will fall down in their respective wells 18. Alternatively, the articles to be coated could be loaded directly into the wells by any suitable manipulating device without need of turning the plates upside down twice. The loaded article-carrying plates 14 are the stacked upon one another by help of the above-mentioned guide pins 31 or shafts, and the whole assembly of plates 12, 14, 16, 44 and 46 are clamped together by means of the circumferentially spaced tie rods 48.

One or more solutions suitable for applying a desired biocompatible coating on the articles located within the wells 18 for making the articles non-thrombogenic is then supplied to the distribution chamber 34 through the inlet opening 32 by means of a pump and a hose (not shown) connected to the inlet. As the pressure acting on the solution in the distribution chamber 34 is uniform over the whole area thereof, the solution will be fed uniformly to the wells 18 in the lowermost plate 14 in parallel vertical flows through the narrow orifices 26 such that a uniform application of the coating on the articles will be ensured. As the solution leaves the wells 18 of the lowermost plate 14, it enters into the space 28 defined by the recess 24 and the bottom side of the next adjacent article-carrying plate 14 and will again be equally distributed in this intermediate space 28 before entering the wells 18 of the next plate 14 via the orifices 26 thereof. The solution may thus be fed successively through all article-carrying plates 14 in parallel, vertical and undisturbed flows and then be returned to an external tank (not shown) via the collection chamber 40 and the outlet opening 42. The same or other solutions may be additionally circulated through the stack of article-carrying plates 14 in order to provide a desired coating on the articles. The finished articles may be unloaded in a similar manner as the loading step, however in the opposite order. Hence, the apparatus and method of the present invention allows for a large number of articles to be properly coated in batches.

It should be noted that the expression "article-carrying plate" used herein and in the claims should be interpreted as "a plate intended for carrying articles".

What is claimed is:

1. An apparatus for coating a plurality of articles in batches, in particular for applying a biocompatible layer on articles adapted to come into contact with blood or body tissue, comprising an article-carrying plate, said article-carrying plate having a top side and a bottom side, a plurality of wells being formed in said top side for receiving therein a respective article to be coated, each of said wells communicating, via a respective orifice, with a space below said bottom side, said orifices having each a cross-sectional flow area that is smaller than the cross-sectional area of each well;

a base plate having an upper surface defining with said bottom side of said article-carrying plate a distribution chamber for receiving and evenly distributing to said orifices a solution containing the coating substance to be applied to said articles, said base plate having an inlet for supplying said solution to said chamber; and a top plate covering said top side of the article-carrying plate and defining therewith a collection chamber for receiving used solution having been flown through said orifices and wells, said top plate having an outlet for discharging said used solution.

2. An apparatus according to claim 1, comprising a first sealing means disposed between said base plate and said article-carrying plate so as to circumferentially seal said distribution chamber, and a second sealing means disposed between said top plate and said article-carrying plate so as to circumferentially seal said collection chamber.

3. An apparatus according to claim 2, wherein said first and second sealing means are O-rings.

4. An apparatus according to claim 1, comprising means for clamping said top plate, said base plate and said article-carrying plate together.

5. An apparatus for coating a plurality of articles in batches, in particular for applying a biocompatible layer on articles adapted to come into contact with blood or body tissue, comprising a plurality of article-carrying plates stacked upon one another, each said article-carrying plate having a top side and a bottom side, a plurality of wells being formed in said top side for receiving therein a respective article to be coated, each of said wells communicating, via a respective orifice, with a space below said bottom side, said orifices having each a cross-sectional flow area that is smaller than the cross-sectional area of each well; a base plate having an upper surface defining with said bottom side of a lowermost of said article-carrying plates a distribution chamber for receiving and evenly distributing to said orifices of said lowermost article-carrying plate a solution containing a coating substance to be applied to said articles, said base plate having an inlet for supplying said solution to said chamber; and a top plate covering said top side of an uppermost of said article-carrying plates and defining therewith a collection chamber for receiving used solution having been flown through said orifices and wells of all article-carrying plates, said top plate having an outlet for discharging said used solution.

6. An apparatus according to claim 5, comprising a first sealing means disposed between said base plate and said lowermost article-carrying plate so as to circumferentially seal said distribution chamber, a second sealing means disposed between said top plate and said uppermost article-carrying plate so as to circumferentially seal said collection chamber, and a third sealing means disposed between adjacent article-carrying plates stacked upon one another so as to circumferentially seal a space between each adjacent pair of article-carrying plates.

7. An apparatus according to claim 6, wherein said first, second and third sealing means are O-rings.

8. An apparatus according to claim 5, comprising means for clamping said top plate, said base plate and said article-carrying plates together.

9. An apparatus according to claim 8, wherein said clamping means comprises at least three circumferentially spaced tie rods.

10. An apparatus according to claim 9, wherein said clamping means further comprises an upper and a lower ring-shaped clamping plate between which said top plate, said article-carrying plates and said base plate are clamped.

11. An apparatus according to claim 5, comprising positioning means between adjacent pairs of said article-carrying plates for fixating said article-carrying plates in a desired mutual rotary position.

12. An apparatus according to claim 11, wherein said positioning means comprise at least two pins on one of said article-carrying plates engaging in corresponding holes in an adjacent one of said article-carrying plates.

13. An apparatus according to claim 5, wherein said wells are arranged in a plurality of concentric circular arrays.

14. An apparatus according to claim 13, wherein said wells are grouped in circle sectors separated by radial, well-free corridors.

15. An apparatus according to claim 5, wherein said wells in adjacent article-carrying plates are located substantially coaxially above one another.

16. An apparatus according to claim 5, wherein opposing top and bottom surfaces of adjacent article-carrying plates define a further distribution chamber for receiving coating solution from the wells of an upstream article-carrying plate of said adjacent plates and for evenly distributing said solution to the wells of a downstream article-carrying plate of said adjacent plates.

17. An apparatus according to claim 5, wherein article-carrying plates of various thickness are stacked upon one another.

* * * * *